United States Patent [19]
Bressler et al.

[11] Patent Number: 5,466,223
[45] Date of Patent: Nov. 14, 1995

[54] NEEDLE ASSEMBLY HAVING SINGLE-HANDEDLY ACTIVATABLE NEEDLE BARRIER

[75] Inventors: Peter Bressler, Philadelphia, Pa.; Niall Sweeney, Rutherford, N.J.; Daniel Hicswa, Carlstadt, N.J.; James A. Burns, Elizabeth, N.J.

[73] Assignee: Becton, Dickinson and Company, Franklin Lakes, N.J.

[21] Appl. No.: 262,806

[22] Filed: Jun. 20, 1994

[51] Int. Cl.$^6$ ................................. A61M 5/00
[52] U.S. Cl. .................. 604/110; 604/198; 604/263
[58] Field of Search .................. 604/198, 192, 604/110, 187, 263, 208, 209, 210

[56] References Cited

U.S. PATENT DOCUMENTS

| | | | |
|---|---|---|---|
| 2,559,474 | 7/1951 | Son | 604/192 X |
| 2,739,591 | 3/1956 | Yochem | 604/210 |
| 4,573,976 | 3/1986 | Sampson et al. | 604/198 |
| 4,738,663 | 4/1988 | Bogan | 604/198 |
| 4,790,828 | 12/1988 | Dombrowski et al. | 604/198 |
| 4,892,521 | 1/1990 | Laico et al. | 604/192 |
| 4,915,696 | 4/1990 | Feimer | 604/192 |
| 4,994,046 | 2/1991 | Wesson et al. | 604/198 |
| 5,026,356 | 6/1991 | Smith | 604/192 |
| 5,215,534 | 6/1993 | DeHarde et al. | 604/198 |
| 5,348,544 | 9/1994 | Sweeney et al. | 604/198 X |

*Primary Examiner*—John D. Yasko
*Attorney, Agent, or Firm*—John L. Voellmicke

[57] ABSTRACT

A needle assembly having a single-handedly activatable needle barrier includes a needle cannula having a proximal end, a distal end and a lumen therethrough connected to a needle hub having an interior cavity in fluid communication with the needle cannula. A guide element is connected to the needle hub and includes an aperture therethrough. An elongate barrier arm having a proximal end and a distal end is provided. The distal end of the barrier arm includes a barrier element having a needle passageway therethrough. The barrier arm is positioned within the aperture of the guide element and the needle cannula is positioned at least partially within the needle passageway of the barrier element. The barrier arm is movable from at least a retracting position wherein the distal end of the needle cannula passes completely through the barrier element so that the distal end of the needle cannula is exposed, to a second extended position wherein the barrier element surrounds the distal end of the needle cannula to prevent incidental contact with the distal end of the needle cannula. Locking means is provided for preventing the movement of the barrier arm from the second extended position.

27 Claims, 13 Drawing Sheets

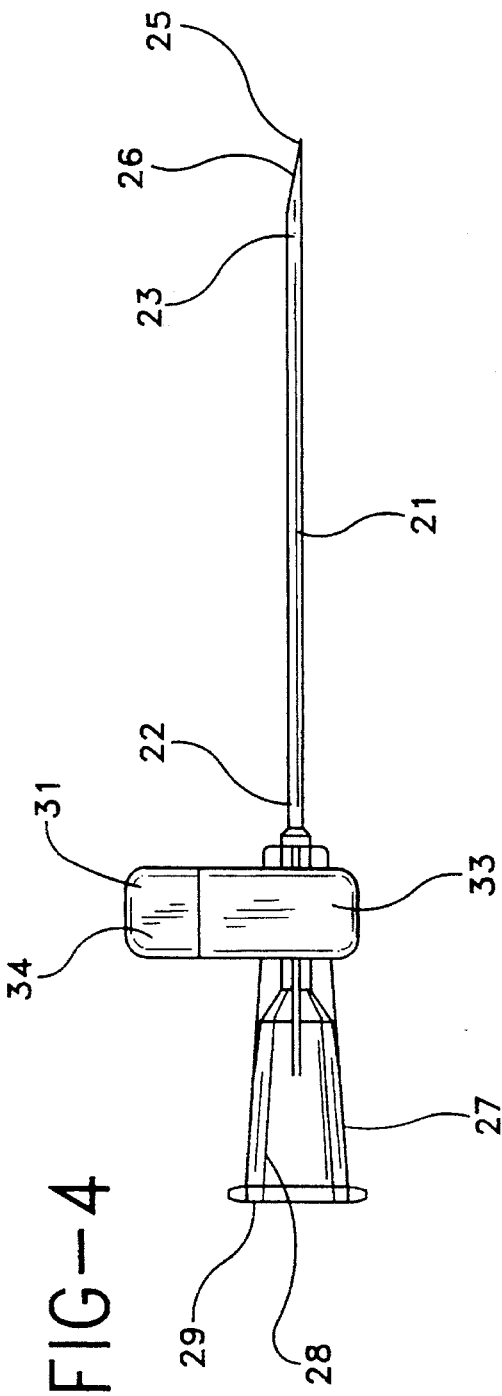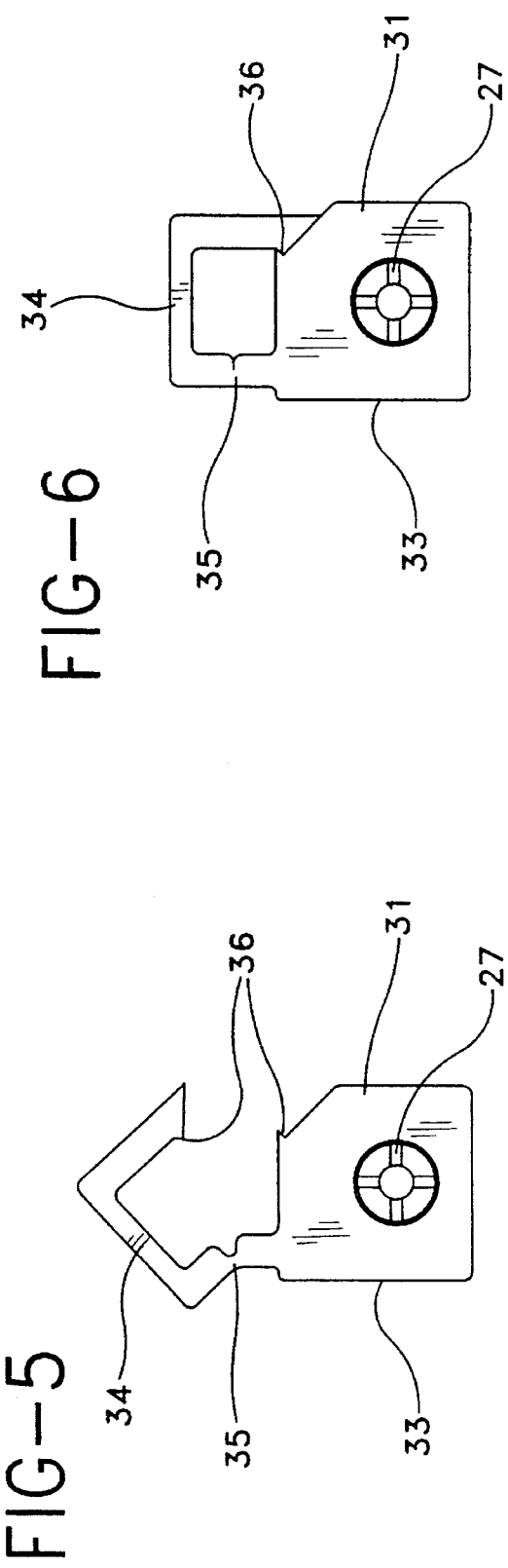

NEEDLE ASSEMBLY HAVING SINGLE-HANDEDLY ACTIVATABLE NEEDLE BARRIER

FIELD OF THE INVENTION

The subject invention relates to safety needle barriers, capable of single-handed activation, for hypodermic needles, blood collection needles, catheter needles and other medical implements for preventing accidental needle sticks.

DESCRIPTION OF THE PRIOR ART

Accidental sticks with a used needle cannula can transmit disease. As a result, the prior art teaches many needle assemblies and medical devices having safety shields which can be positioned to prevent accidental contact with the needle point after use of the medical device. Some prior art safety shields define a rigid cylinder which can be telescoped in a proximal direction over a used needle cannula. These devices are effective however they require a two-handed procedure wherein the healthcare worker holds the medical instrument with one hand and manually advances the needle shield with the other hand. Needle shields of this type, which fit over syringe barrels, are also expensive because each separate size syringe barrel must have its appropriately sized shield.

In addition to needle shielding devices which require two-handed operation, the prior art also teaches needle shielding devices which are automatic and do not require one-handed or two-handed activation. These needle shield assemblies also have important deficiencies. Most notably, the shield can be activated unintentionally thus rendering the unused instrument unsuitable for its intended purpose. Also many procedures wherein needles and hypodermic syringes are used the needle is first used to pierce a vial stopper to draw medication into the syringe and then used to inject the medication into the patient. However, automatically activatable needle shields can be activated during the filling operation and render the medication undeliverable. Some automatic safety shields, in their initial position, cover the tip of the needle making it difficult for the healthcare worker to see precisely where the needle will be placed in the patient and/or the depth of penetration of the needle into the patient. This is particularly problematical where the needle is being used to draw blood or to enter a vein for the purpose of delivering medication. Also, some of the automatic devices initially cover the needle tip making the needle look like it is safely protected when the shield will provide no resistance to incidental contact and even its uncontaminated state can be an instrument to provide a painful puncture wound to an unsuspecting user.

Other prior art needle shielding devices include a small housing which sides along the needle to the distal point where the shield locks in place about the needle. These devices are compact in size but are usually assembled over the needle tip which presents manufacturing problems. Specifically the needle of a hypodermic syringe has finely ground, delicate cutting edges which can be damaged by the initial assembly operation which requires installing the needle shield over the tip of the needle. A damaged needle point can cause patient discomfort and make the needle difficult to use when piercing rubber-stoppered medication-containing vials.

Although the prior art teaches many needle shielding structures there is still need for a simple, straight-forward, reliable, easily fabricated needle assembly which is self-contained, capable of single-handed activation, and can be used with a variety of medical instruments. There is also a need for a needle barrier which may be assembled to the side of a needle cannula without passing over the sharp and delicate needle tip during the assembly process.

SUMMARY OF THE INVENTION

The subject invention is directed to a needle assembly having a single-handedly activated needle barrier. The needle assembly includes a needle cannula having a proximal end, a distal end and a lumen therethrough. A needle hub having an interior cavity terminating at an open proximal end of the hub is connected to the needle cannula so that the lumen of the cannula is in fluid communication with the interior cavity of the hub. A guide element is connected to the hub and includes an axially oriented aperture therethrough. An elongate barrier arm having a proximal end and a distal end is provided. The distal end of the barrier arm includes a barrier element having a distal end, a proximal end and a needle passageway therethrough. The barrier arm is positioned within the aperture of the guide element and the needle cannula is positioned at least partially within the needle passageway of the barrier element. The barrier arm is movable from at least a first retracted position wherein the needle cannula passes through the barrier element so that the distal end of the needle cannula is exposed, to a second position where the barrier element surrounds the distal end of the needle cannula to help prevent accidental contact with the distal end of the cannula. Locking means are provided for preventing the movement of the barrier arm from the second extended, needle protecting, position. A finger contact surface is provided on the barrier arm for applying digital pressure to the barrier arm to move the barrier arm into the second extended position.

The present invention also includes features for allowing the assembly of the barrier element to the needle cannula from the side of the needle cannula without passing the needle cannula through the barrier element during assembly. Such assembly is accomplished by providing a longitudinal slot in the side of the barrier element extending outwardly from the needle passageway. Side assembly can also be accomplished with a needle barrier having a first longitudinal slot extending outwardly from the needle passageway, a second longitudinal slot opposed from the first longitudinal slot and extending outwardly from the needle passageway, and a transverse slot connecting the first and second longitudinal slots and extending outwardly from the needle passageway. Assembly is accomplished by placing the needle cannula in the transverse slot and rotating the barrier element with respect to the needle cannula until the needle cannula enters and passes through the first and second longitudinal slots into the needle passageway of the barrier element.

BRIEF DESCRIPTION OF THE DRAWINGS

FIG. 4 is a side-elevational view of the needle cannula, needle hub and guide element.

FIGS. 5 and 6 are side-elevational views of the distal end of the assembly of FIG. 4. FIG. 5 illustrates the two-piece guide element having a living hinge wherein the cap portion of the guide element is in the open position. FIG. 6 illustrates the cap portion of the guide element in the closed position.

DETAILED DESCRIPTION

Figure 1:
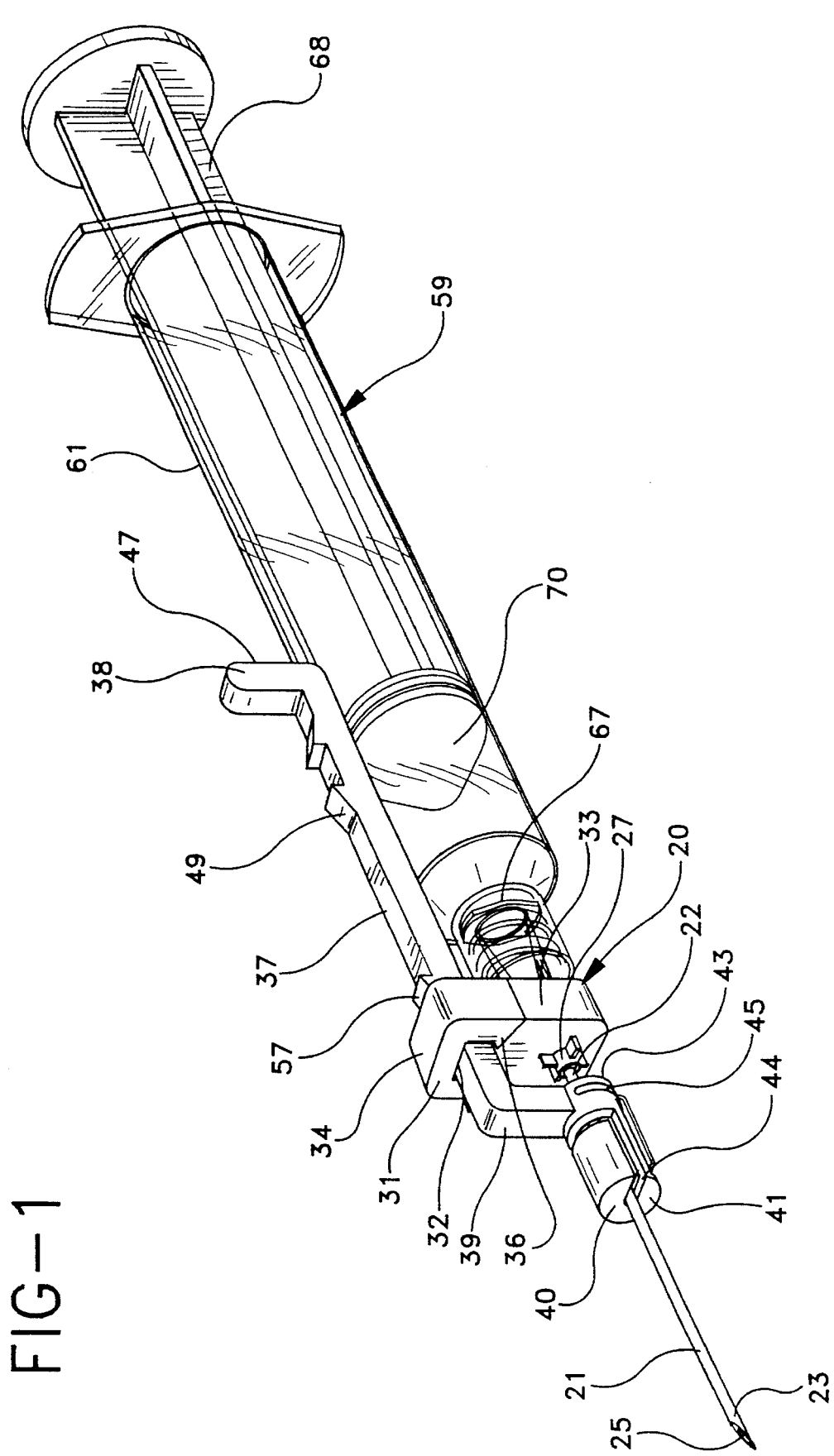
FIG. 1 is a perspective view of the needle assembly having a single-handedly activatable needle barrier, attached to a hypodermic syringe.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1–9 a needle assembly 20 having a single-handedly activated needle barrier includes a needle cannula 21 having a proximal end 22, a distal end 23 and a lumen therethrough. Distal end 23 includes sharpened distal tip 25. A needle hub 27 having an interior cavity 28 which terminates at an open proximal end 29 of the hub, is connected to the proximal end of needle cannula 21 so that the lumen is in fluid communication with the interior cavity of the hub. In this preferred embodiment, interior cavity 28 is frusto-conically shaped.

A guide element 31 is connected to the needle hub and includes an aperture 32. In this embodiment, the guide element is attached to the needle hub through the use of any suitable joining technique such as adhesives, ultrasonic welding and the like. For low volume production attaching the guide element to an existing hub is desirable from a cost standpoint. It is within the purview of the present invention to include an integrally molded one-piece hub and guide element. For high volume production it is preferred that the needle hub and guide element be of one-piece integrally molded thermoplastic. The aperture in the guide element is axially oriented and dimensioned to accept an elongate barrier arm 37, as will be described in more detail hereinafter. The elongate barrier arm includes a proximal end 38 and a distal end 39. The distal end of the barrier arm includes barrier element 40 having a distal end 41, a proximal end 43 and a needle passageway 44 therethrough. The elongate barrier arm, including the barrier element, is preferably integrally molded of the same material. However the barrier element and the barrier arm can be separately formed and joined together by any suitable means such as adhesive, ultrasonic welding and frictional or snap-fit type engagement. The barrier arm and barrier element can also be separately formed and connected by a separate element such as a metal clip which can allow the barrier element to move or orient itself slightly with respect to the barrier arm to allow relatively unstressed alignment of the needle cannula longitudinal axis with the longitudinal axis of the needle passageway as the barrier element moves along the cannula in a manner which will be described hereinafter. The barrier arm is positioned within aperture 32 of guide element 31 and needle cannula 21 is positioned within needle passageway 44 of barrier element 40. The aperture of guide element 31 is dimensioned and oriented to accept the elongate barrier arm.

Figure 2:
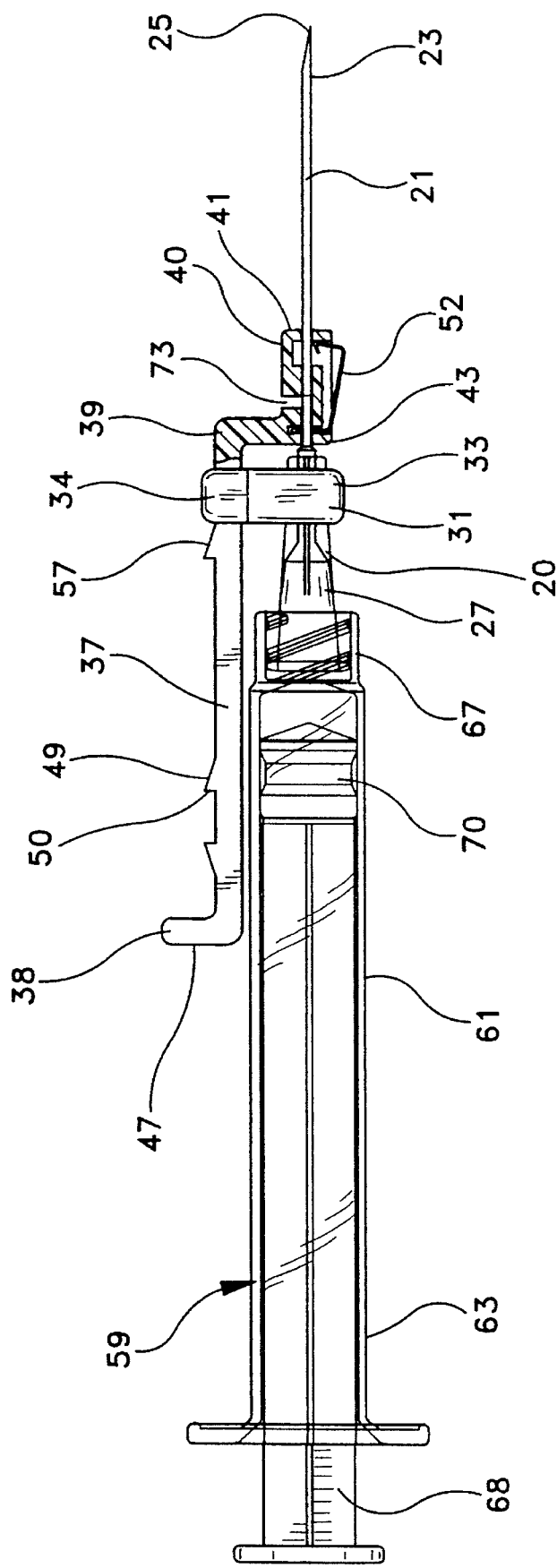
FIG. 2 is a partially cross-sectioned side-elevational view of the syringe and needle assembly of FIG. 1 illustrating the elongate barrier arm in the first retracted position.
Figure 3:
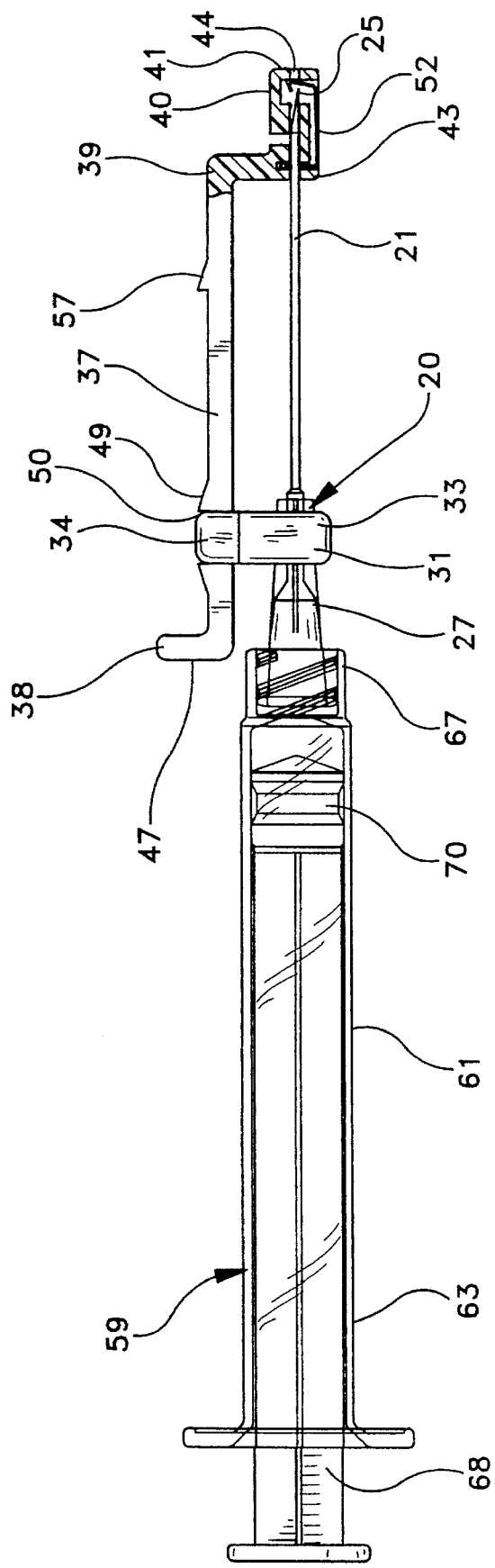
FIG. 3 is a partially cross-sectioned side elevational view of the syringe and needle assembly of FIG. 1 illustrating the elongate barrier arm in the second extended position.
Figure 7:
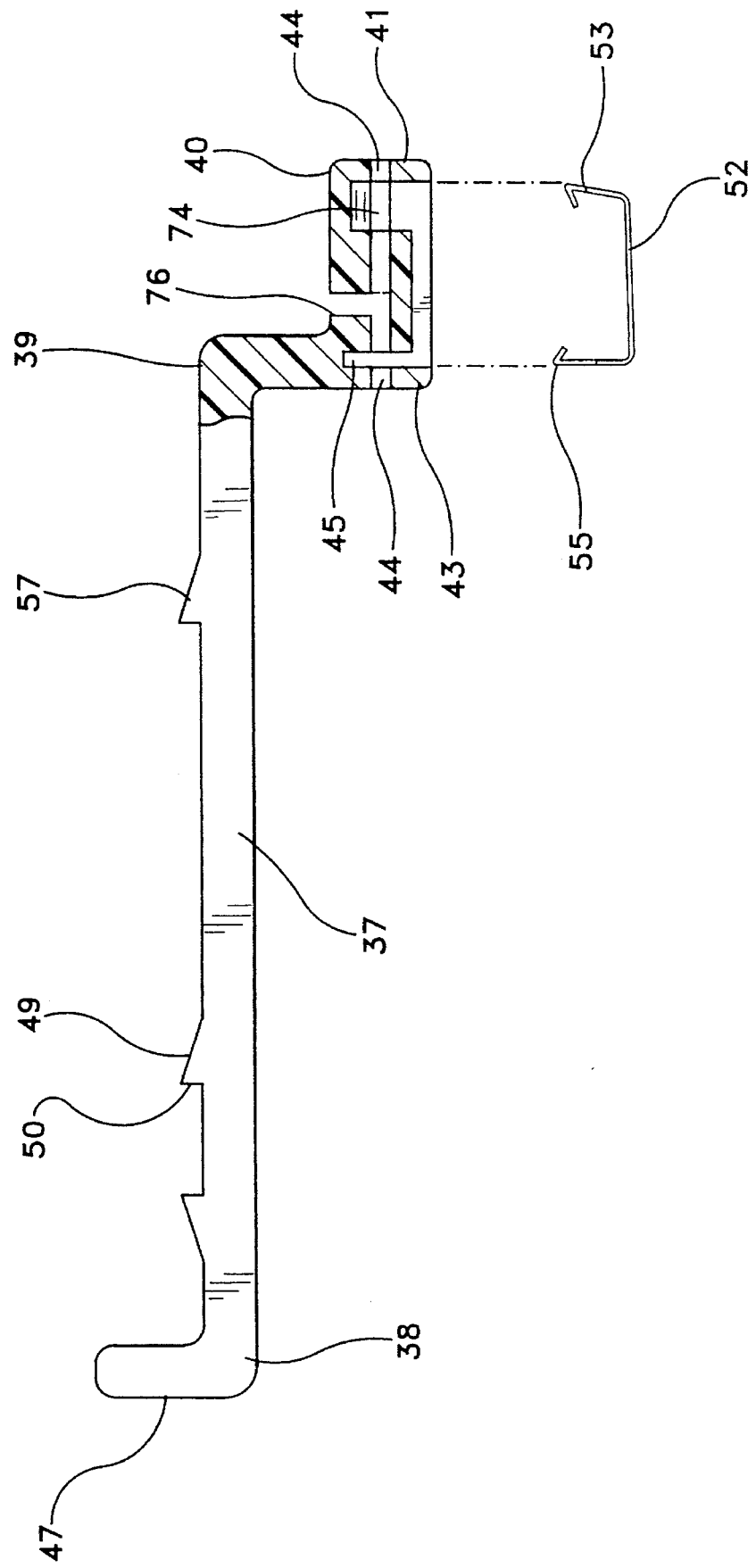
FIG. 7 is a partially cross-sectioned exploded side-elevational view of the elongate barrier arm of the present invention.
Figure 8:
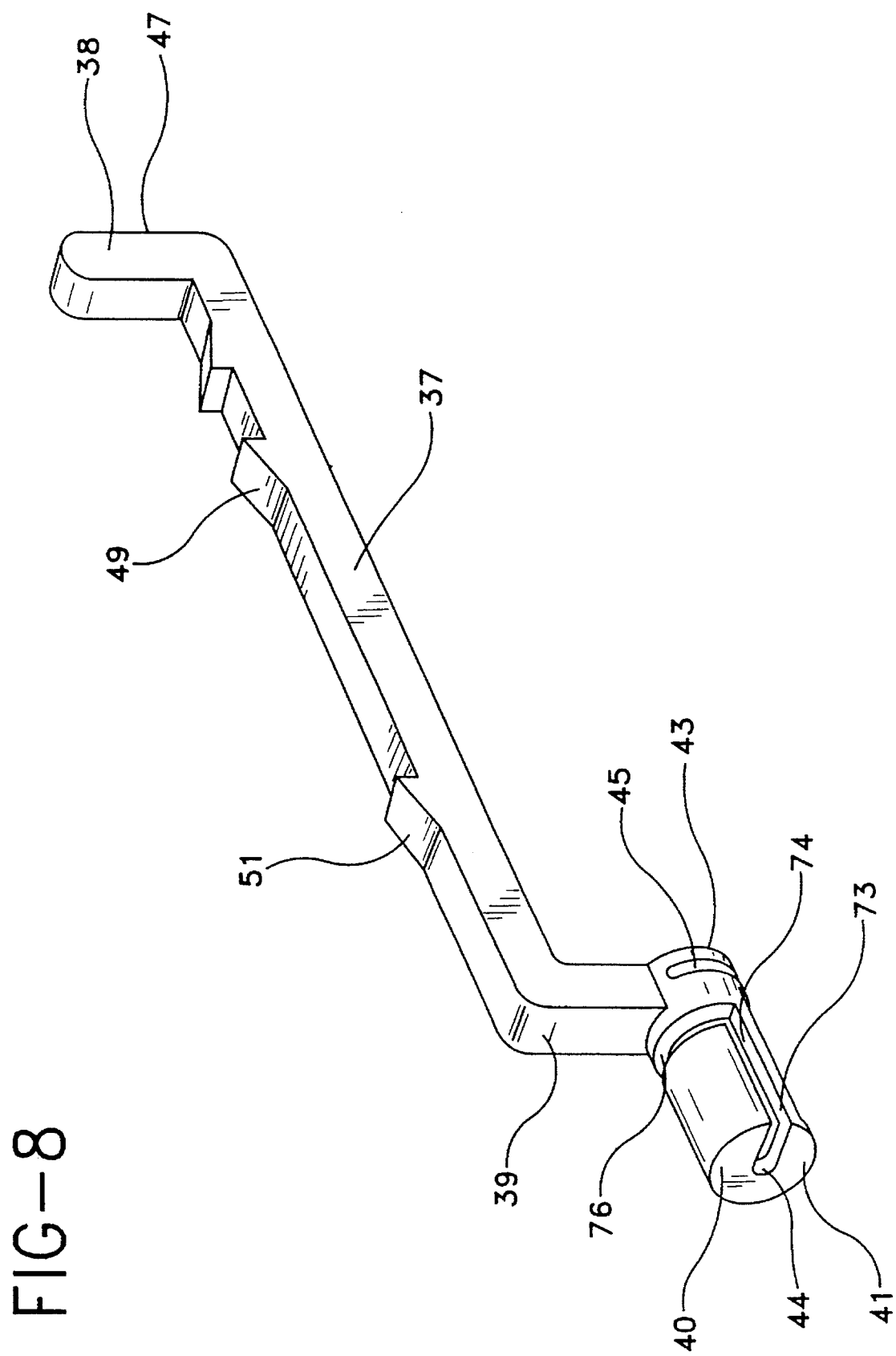
FIG. 8 is a perspective view of the elongate barder arm of the present invention.
Figure 9:
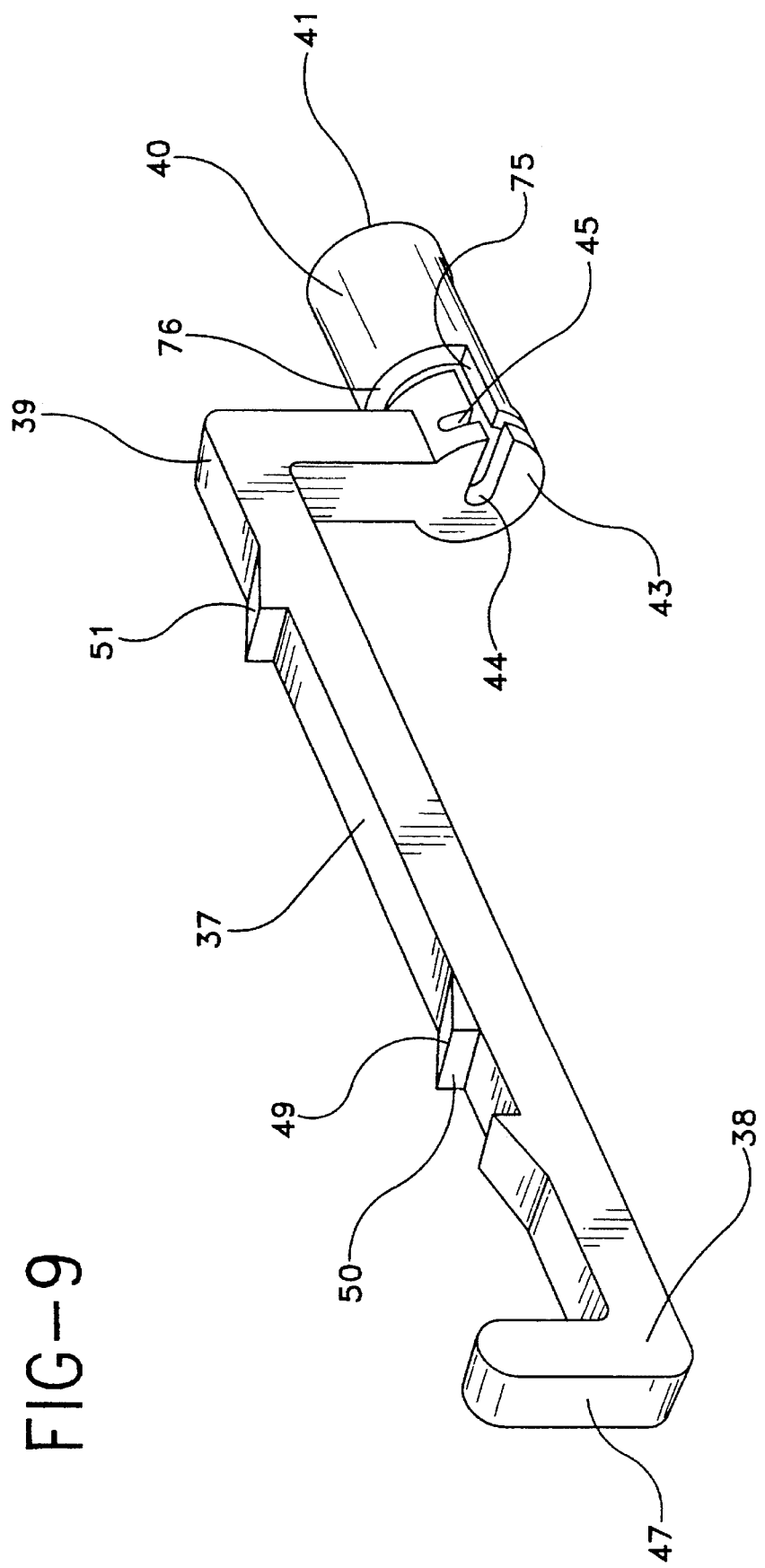
FIG. 9 is a perspective view of the elongate barder arm of the present invention showing the opposite side of the barrier arm of FIG. 8.

Elongate barrier arm 37 is movable from at least a first retracted position, as best illustrated in FIG. 2, wherein distal end 23 of the needle cannula passes completely through the barrier element so that the distal end of the needle cannula is exposed, to a second position, as best illustrated in FIG. 3, wherein the barrier element surrounds distal end 23 and sharpened distal tip 25 of the needle cannula to prevent accidental contact with the distal end of the needle cannula.

The barrier arm includes a finger contact surface to allow the single-handed movement of the barrier arm from the first retracted position of FIG. 2 to the second extended position of FIG. 3. In this preferred embodiment, finger contact surface 47 is provided on the proximal end of the elongate barrier arm. This position for the finger contact surface is preferred because it is the farthest position from the sharp needle tip. The barrier arm, as best illustrated in FIGS. 1–3, can be single-handedly advanced from the first retracted position to the second extended position by holding the syringe in one hand and pushing on finger contact surface 47 with the thumb of the holding hand. The ability to allow single-handed operation is an important feature of the present invention since it allows the person administering the injection to use the other hand for other purposes such as applying pressure to a vein to prevent bleeding.

An advantage of the present invention is that one needle assembly can be sized so that it can be used with several different sizes of syringes, for example syringes having 3 ml and 5 ml volume capacities. A locking means is provided for preventing the movement of the barrier arm proximally from the second extended position of FIG. 3. The preferred embodiment includes two locking means. The first locking means includes a projection on the barrier arm configured to allow the barrier arm to pass through the aperture in the guide element in a distal direction but not in a proximal direction. In the preferred embodiment this projection is locking ramp 49 which is a wedge-shaped projection on the barrier arm which is larger at its proximal end than at its distal end. The proximal end of locking ramp includes locking wall 50. After the locking wall passes through the guide element aperture, upon distal motion of the barrier arm, the locking wall prevents proximal motion of the barrier arm with respect to the guide element and locks the barrier element in the needle protecting position. It is preferred to shape and size the elements of the locking means, such as ramp 49, so that there is an audible indication and/or an abrupt tactile feel to indicate that the barrier arm is in its second extended locked position. Undercutting ramp 49 so that it snaps or springs outwardly after passing through the aperture of the guide element is one way to produce an audible clicking sound.

Second locking means provided in this preferred embodiment is spring clip 52. Spring clip 52 is preferably made of a resilient material which is resistant to being pierced by the sharp needle tip. Spring clip 52 is preferably made of spring steel or stainless steel sheet and is mechanically connected to the barrier element so that a transverse arm or portion 53 of the spring slip is biased to press against needle cannula 21. When the elongate barrier arm is moved to the second extended position transverse portion 53 of spring clip 52 falls into a position at least partially covering distal end of the needle to prevent movement of the barrier element in a proximal direction with respect to the needle cannula.

It is not necessary that both the locking ramp and the spring clip be used to prevent proximal motion of the barrier element from the second extended position. Either locking means may be used alone without the other. It is within the purview of the instant invention to include any structural cooperation between the barrier element and the elongate barder arm which will prevent proximal motion of the barrier arm after it reaches the second extended position. Preferably, this structure can be molded into the components to lower cost. However, separate elements such as metal spring clips may be used to prevent proximal motion. Likewise, it is within the purview of the instant invention to include any locking means in the barder element which can grab the needle cannula to prevent proximal motion of the barrier element. A spring clip having a transverse portion is preferred because of its mechanical simplicity and low cost. More complicated spring-loaded clips which grab the cannula side wall, or a projection or detent in the cannula side wall, are also within the purview of the instant invention.

It is preferable to configure the needle assembly so that the elongate barrier arm is releasably held in the first retracted position, as illustrated in FIG. 3, so that it will not move accidentally during the injection process. Any structural configuration that will provide an additional frictional resistance to forward motion will suffice as a means for releasably holding the barrier arm in the first retracted position. This result can be achieved by enlarging one of the cross-sectional dimensions of the barrier arm at its distal end so that the enlarged portion of the barder arm frictionally engages the aperture in the guide element when the barrier arm is in the first retracted position. Digital pressure applied to contact surface 47 can overcome the frictional interference fit and allow the barrier element to move distally along the needle cannula. The barrier arm can be shaped so the frictional force gradually decreases with distal motion with respect to the guide element in order to avoid an abrupt release of the barrier arm.

Means for releasably holding the barrier arm in the first retracted position, in this preferred embodiment, includes a protuberance 57 on the distal end of the barrier arm which is shaped and sized so that distal force must be applied to the elongate barrier arm to force the portion of the barrier arm containing the protuberance through the aperture.

As best illustrated in FIG. 4, sharpened distal tip 25 of needle cannula 21 is produced by grinding the distal tip at a angle to produce angled beveled edges 26. When using the needle cannula to enter a vein for the purpose of delivering medication or withdrawing blood it is desirable to have the beveled edge facing outwardly when penetrating the vein. In a small diameter needle the bevel is often difficult to see easily. The present invention can be configured so that, as illustrated in FIG. 4, the guide element aperture, and accordingly, the elongate barrier arm, are on the same side of the needle cannula as the beveled edge. Accordingly, the healthcare worker will know the orientation of the needle bevel by observing the position of the elongate barrier arm. This advantage is possible because the preferred embodiment only has a singular barrier arm which can be positioned at a predetermined relationship with respect to the needle bevel.

Although the needle assembly of the present invention is suitable for use with a wide variety of medical devices, including blood collection devices, it is illustrated in FIGS. 1–3 as being used with hypodermic syringe 59. Syringe 59 includes syringe barrel 61 having an elongate cylindrical body defining a chamber 62 for retaining fluid. The barrel includes open proximal end 63, a distal end 64 and a frusto-conically shaped tip extending from the distal end having a passageway therethrough in fluid communication with the chamber. The frusto-conically shaped tip of the syringe frictionally engages the frusto-conically shaped cavity of the needle hub. In this embodiment, the syringe barrel also includes a locking luer-type collar 67 which is known in the art and further improves the connection between the needle hub and the syringe barrel through interaction of internal screw threads on the collar and projections on the needle hub. For the purpose of drawing fluid into and out of chamber 62 the hypodermic syringe includes an elongate plunger 68 having a distal end 69 having a stopper 70 which is in fluid-tight slidable engagement with the interior of the chamber.

It is also within the purview of the present invention to include a needle hub which is integrally molded with a syringe barrel made of thermoplastic or glass. In this configuration, the tip of the syringe barrel which extends from the distal end of the barrel and the needle hub are one in the same element. In this configuration, the needle is preferably attached to the needle hub/syringe tip through the use of an adhesive so that the needle cannot be removed from the syringe barrel. This configuration is ideally suited for pre-filled syringes which are usually made with a permanently attached needle cannula.

To facilitate the assembly of the needle assembly it is preferred that guide element 31 include a main body portion 33 and a cap portion 34 which together define aperture 32. In the preferred embodiment, cap portion 34 and main body portion 33 of the guide element are connected through living hinge 35. During assembly, as will be discussed in more detail hereinafter, the elongate barrier arm may be placed in contact with main body portion 33, and cap portion 34 is then rotated to the shut position as best illustrated in FIG. 6. The cap portion remains in the shut position due to a cooperating locking structure between the cap portion and the main body portion which is generally illustrated by numeral 36.

The two-piece structure of the guide element, connected by living hinge, is a preferred structure. A one-piece guide element is also within the purview of the invention as the parts can be designed for assembly by providing a different location for the finger contact surface such as distally of the guide element or providing a two-piece barrier arm which is assembled after part of the barrier arm is in the aperture. Also, the aperture in the guide element can be positioned at a distance from the needle cannula so that the barrier arm far enough away from the needle to allow the user of the needle assembly on medical devices of various sizes and outside diameter.

The barrier element requires only a needle passageway so that it can move freely along the length of the needle cannula. However, assembly of such a device could require initially passing the barrier element over the sharp distal point of the needle, before installing spring clip 52. Such an assembly process runs the risk of damaging the needle point or embedding the needle point in the barrier element during assembly. Also, the equipment must be very precise to align the very small needle cannula and the needle passageway of the barrier element. To avoid more costly assembly equipment and the cost of scrapping damaged product the barrier element may be designed with a slot running along its side so that the element may be placed on the needle cannula by lateral motion distally of the sharp point and thus avoiding any damage to the point. The spring clip can then be designed to cover part of the horizontal slot to prevent the needle from moving back out of the slot during operation.

In addition to the one-slot barrier element described hereinabove, the preferred embodiment of the present invention includes a three-slot arrangement. In particular, barrier element 40 includes a slot arrangement 73 having a first longitudinal slot portion 74 extending outwardly from needle passageway 44. First longitudinal slot portion 74 extends from distal end 41 of the barrier element, but not completely to proximal end 43. A second longitudinal slot portion 75 is positioned on the opposite side of the barrier element, opposed from said first longitudinal slot portion, and extends outwardly from the needle passageway. The second longitudinal slot portion begins at proximal end 43 of the barrier element and extends distally but not completely to the distal end of the barrier element. Transverse slot portion 76 connects the first longitudinal slot portion and the second longitudinal slot portion and extends outwardly from the needle passageway.

Figure 10:
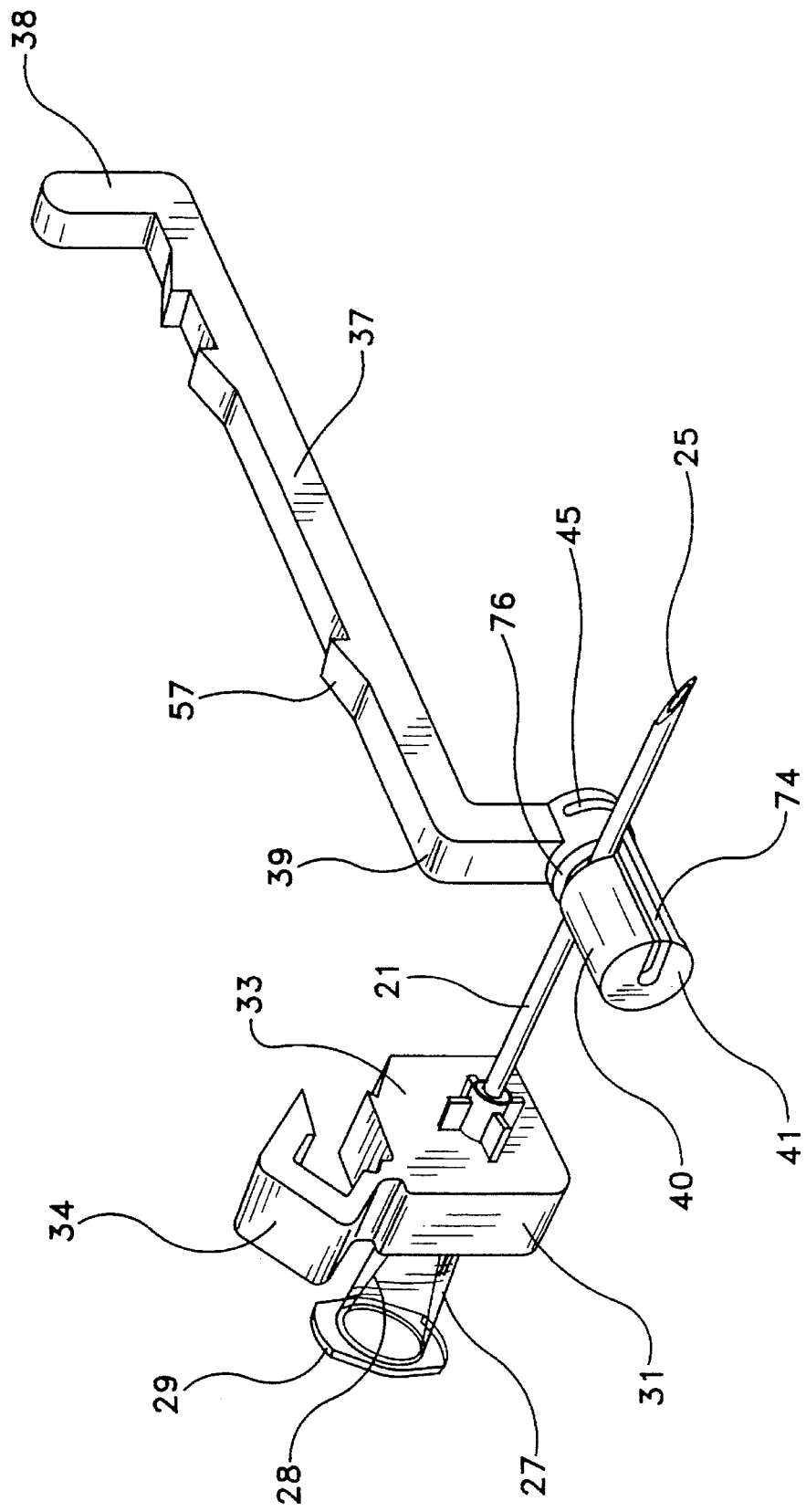
FIGS. 10–12 illustrate the assembly of the needle assembly having single-handedly activatable needle barder.
Figure 11:
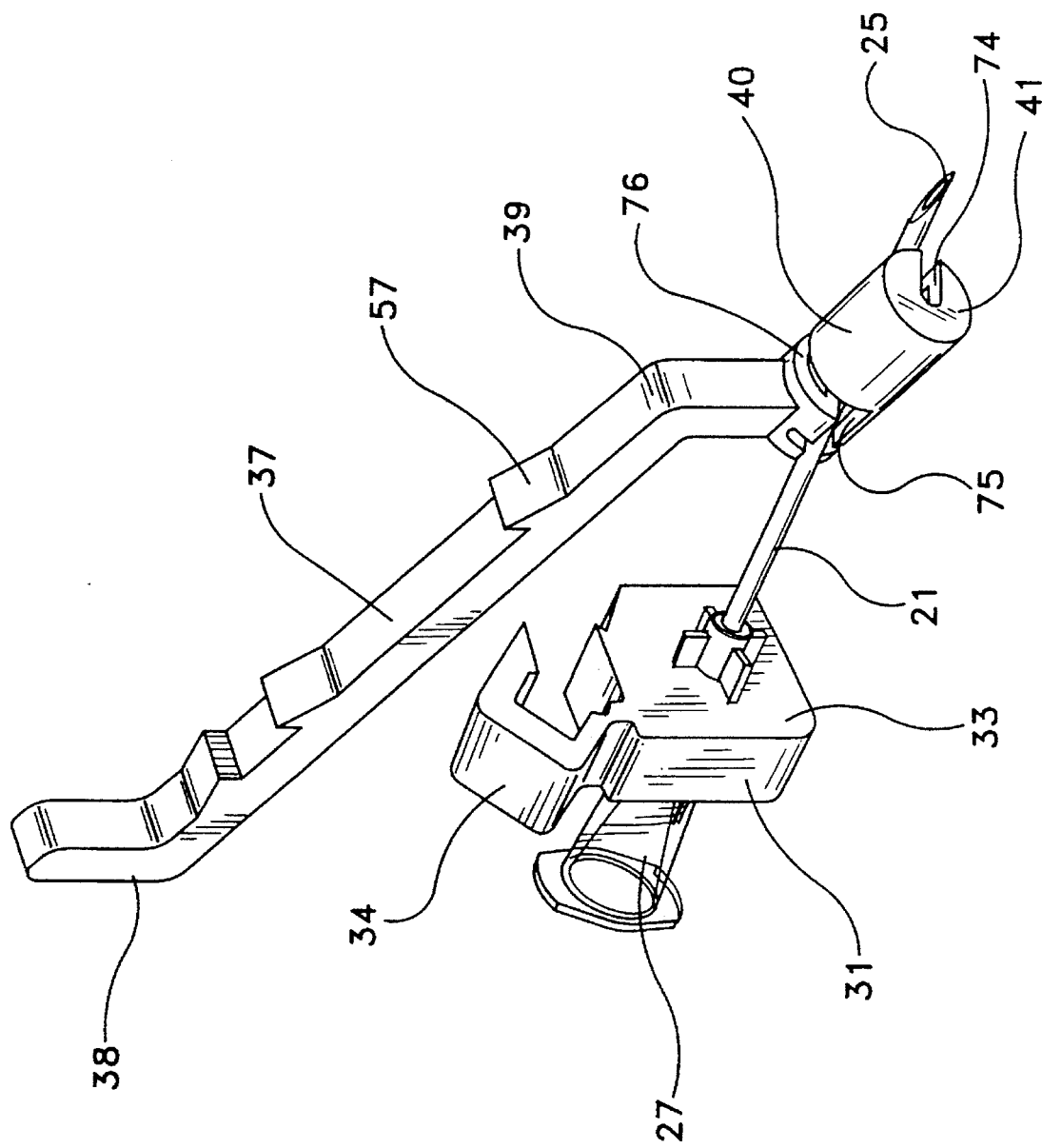
Figure 12:
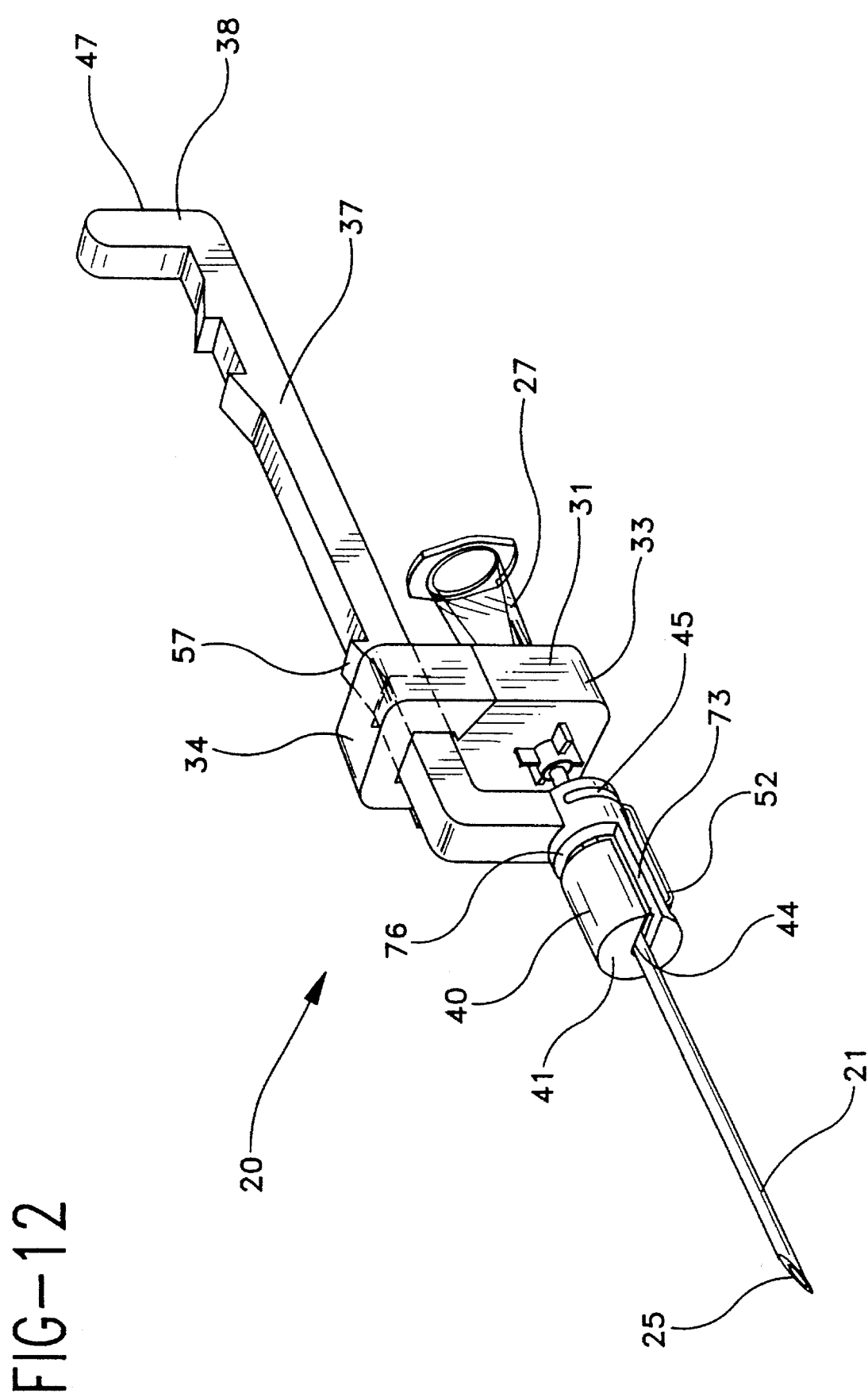

The barrier element of the preferred embodiment, because of its unique slot arrangement, can easily be assembled to the other elements of the needle assembly from the side of the needle cannula without being passed over sharpened distal tip 25 of the needle cannula. Assembly, as best illustrated in FIGS. 10–12 assembly proceeds as follows. Needle cannula 21 and elongate barrier arm 37 are oriented so that the needle cannula is positioned within transverse slot portion 76 of slot arrangement 73, as best illustrated in FIG. 10. Next, the needle cannula and the barrier element are rotated with respect to each other so that the needle cannula enters and passes through first longitudinal slot portion 74 and second longitudinal slot portion 75, as best illustrated in FIG. 11. The relative rotation of the needle cannula with respect to the barrier element continues until the needle cannula is in needle passageway 44 of the barrier element, as illustrated in FIG. 12. It should be noted that the barrier element cannot come off the needle laterally unless it is rotated back to the position where the needle cannula is in the transverse slot. At this time, the elongate barrier arm is positioned next to the main body portion 33 of the guide element and cap portion 34 of the guide element is engaged with main body portion 33 to form the assembled guide element having the elongate barrier arm within aperture 32. In the preferred embodiment this step is accomplished by rotating the cap portion about living hinge 35 until it locks to the main body portion, through cooperative structure in the cap portion and the main body portion.

After the barrier element and the needle cannula are joined, in this preferred embodiment, the barrier clip 52 is assembled to barrier element 40. In the preferred embodiment barrier element 40 includes grooves 45, on each side of the barrier element, which are sized and shaped to frictionally engage barbed proximal end 55 of barrier clip 52. Although, in the preferred embodiment, the barrier clip is not assembled to the barrier element until after the needle cannula is in position, the barrier clip and barrier element are shown in the exploded view of FIG. 7 to illustrate the relationship between these two elements. It is within the purview of the instant invention to include configurations wherein the barrier clip is assembled before the needle cannula is placed in the barrier element aperture. These structures may require the temporary biasing of the transverse arm 53 of the spring clip to allow proper assembly. Barbed proximal end 55 of the barrier clip is split into two sections which straddle the needle passageway in the barrier element. Also, in an embodiment which only includes a side aperture the straddling structure of the barrier clip will be necessary to hold the needle in a coaxial relationship with the needle passageway. Barrier clip 52 includes transverse arm or portion 53 which is biased to contact the side of the cannula until the barrier arm reaches its second extended position wherein the transverse portion of the clip falls into a position which at least partially covers the distal end of the needle, as illustrated in FIG. 3, for preventing movement of the barrier element in a proximal direction with respect to the needle cannula.

When using the needle assembly of the present invention with medical devices having a primed scale and/or volume measuring indicia, such as a syringe, it is preferred that the elongate barrier arm be formed of a transparent thermoplastic material. The use of transparent material will allow the user to read the scale or volume measuring indicia through the barrier arm. Likewise, the barrier arm may have a curved shape to conform to the outside diameter of the syringe barrel so that scale visualization through the transparent barrier arm is easier and there is less structure projecting from the syringe or away from the medical device to interfere with the medical procedure for which the needle assembly is being used.

Figure 13:
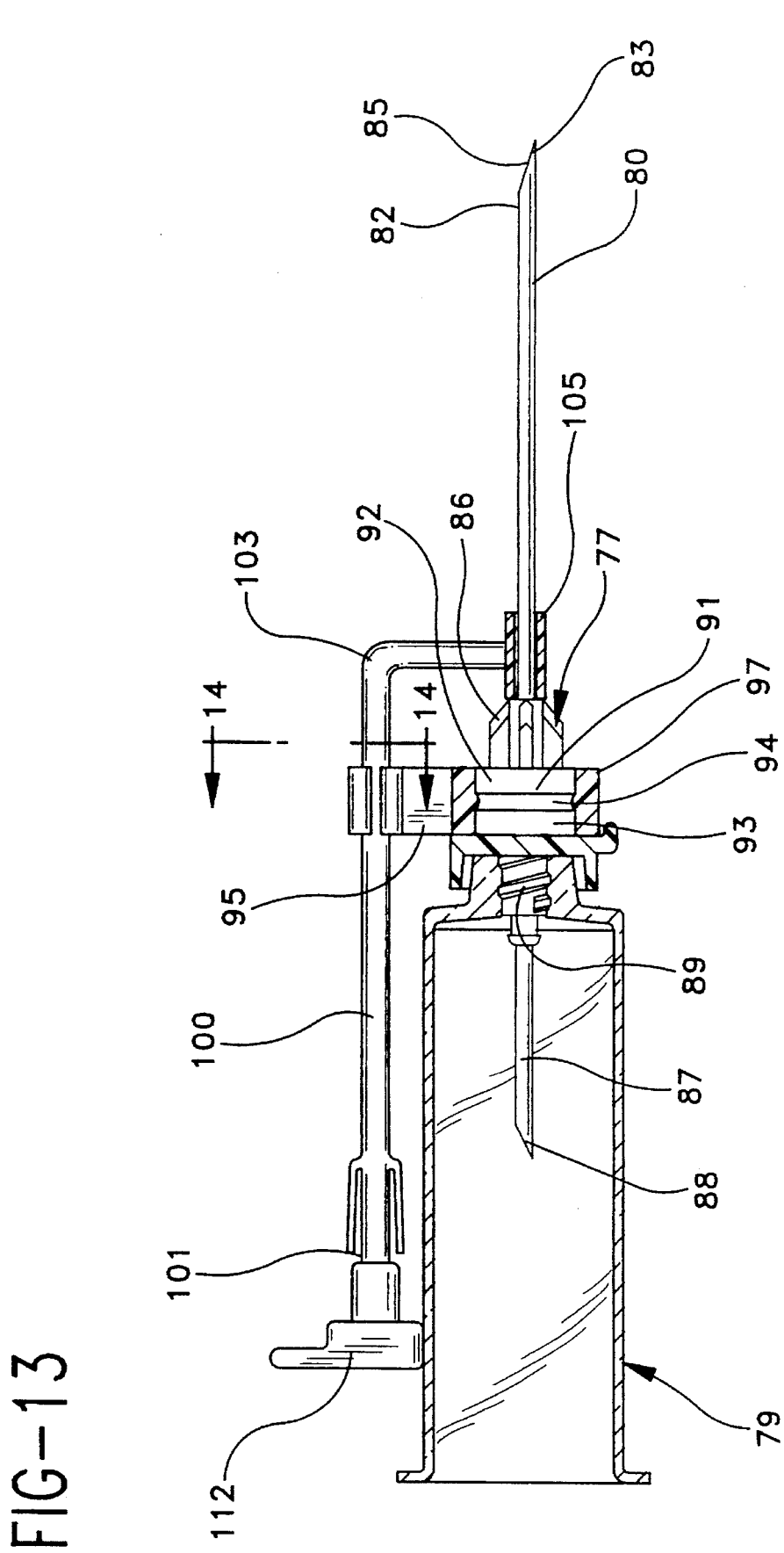
FIG. 13 is a partially cross-sectioned side-elevational view of an alternative embodiment of the needle assembly having a single-handedly activatable needle barrier, attached to an evacuated blood collection tube holder and having the elongate barrier arm in the first retracted position.
Figure 14:
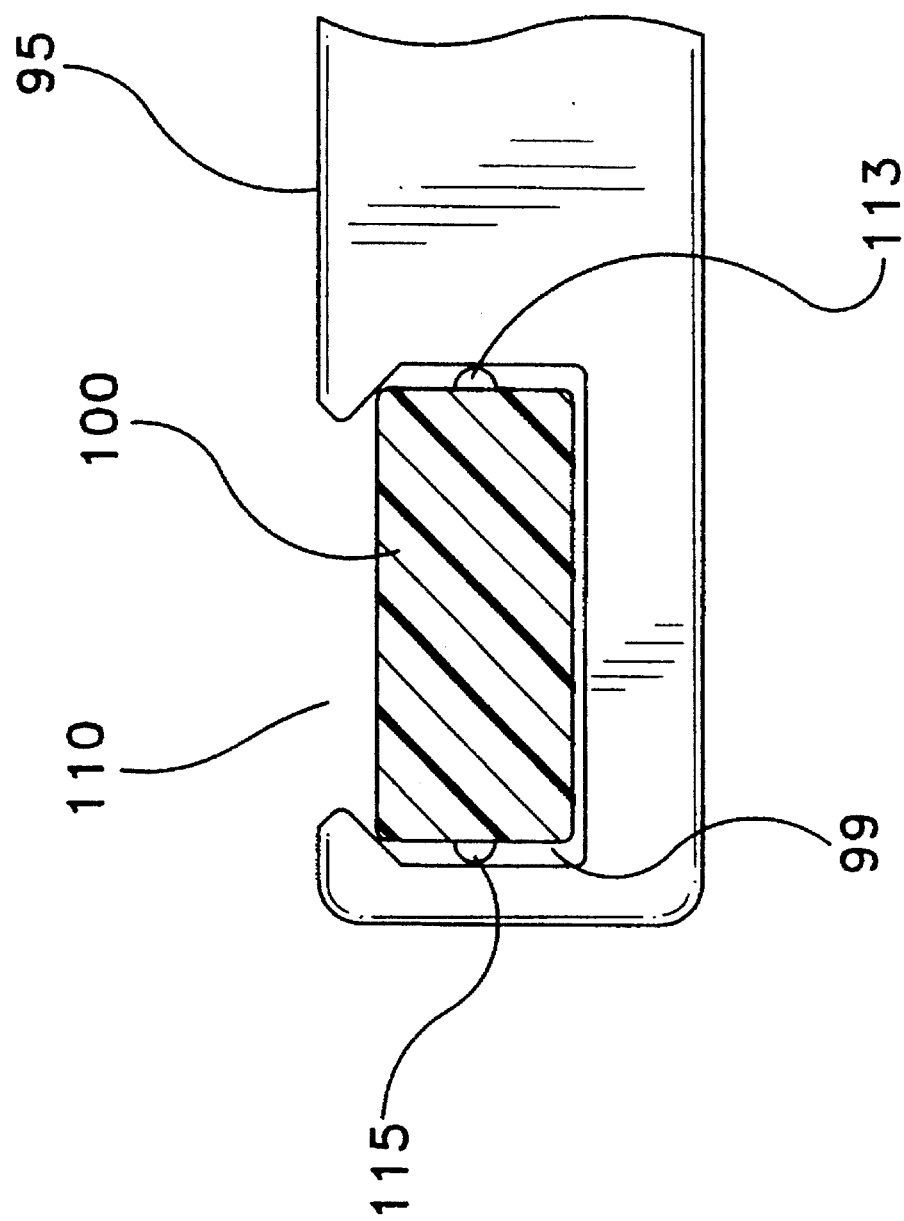
FIG. 14 is a cross-sectional view of the needle assembly of FIG. 13 taken along line 14—14.
Figure 15:
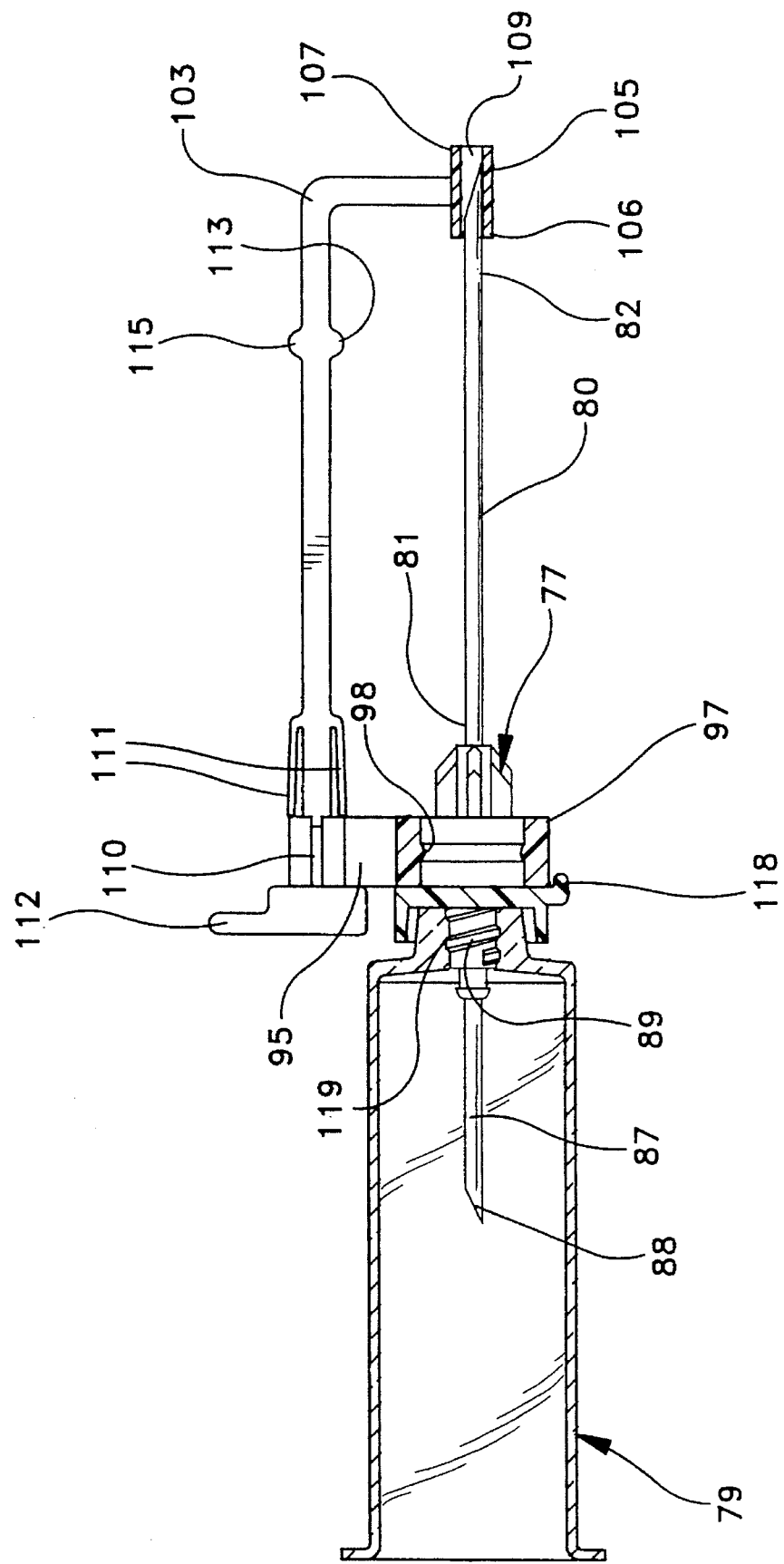
FIG. 15 is a side-elevational view of the needle assembly and evacuated tube holder of FIG. 13 illustrating the elongate barder arm in the second extended position.

Referring to FIGS. 13–15, an alternative needle assembly 77 is attached to prior art evacuated tube holder 79. Needle assembly 77 includes distally facing needle cannula 80 having a proximal end 81 and a distal end 82 and a lumen therethrough. Distal end 82 includes a sharpened distal tip 83 having beveled cutting edge 85. A needle hub 86 includes an interior cavity which terminates at tip 88 of proximally inwardly facing needle cannula 87. It is within the purview of the present invention to include a separate distally facing needle cannula and proximally facing needle cannula connected to the hub and communicating with each other through an internal cavity in the hub. It is also within the purview of the present invention to include a hub connected to a single needle cannula comprising a distally facing needle cannula portion and a proximally facing needle cannula portion passing directly through the hub so that the needle cannula itself forms the interior cavity of the hub. Interior cavity as used in this invention, is intended to include any passageway which allows the lumen of the distally facing cannula to communicate with apparatus to be connected on the proximal side of the hub. Needle hub 86 also includes proximally located threaded portion 89 and beating surface 91. In this embodiment beating surface 91 includes a distal portion 92, a proximal portion 93, and annular groove 94 therebetween. The beating surface in this embodiment is located distally of the threaded portion.

A guide element 95 includes a collar 97 which frictionally and rotationally engages the bearing surface 91 of needle hub 86. Collar 97 includes an interior surface having an inwardly facing annular projection 98. In this embodiment guide element 95 is attached to needle hub 86 by a forced snap fit which causes annular projection 98 of the guide element collar to engage groove 94 of the bearing surface.

This arrangement allows the guide element to be forcibly rotated around the needle hub but prevents the guide element from moving axially with respect to the needle hub. The reason for allowing rotational motion of the guide element with respect to the needle hub will be explained in more detail hereinafter. Guide element 95 also includes aperture 99 therethrough.

An elongate barrier arm 100 includes a proximal end 101 and a distal end 103. Distal end 103 includes cylindrically-shaped barrier element 105 having a proximal end 106, a distal end 107 and a needle passageway 109 therethrough. Aperture 99 in guide element 95 is axially oriented and dimensioned to accept elongate barrier arm 100. In this embodiment the guide element includes a gap 110 positioned to intersect aperture 99 so that the portion of the guide element defining the aperture does not completely surround the elongate barrier arm. In this embodiment, the portion of the aperture defining the gap and the elongate barrier arm are configured so that the barrier arm may be laterally snapped into the aperture during the assembly of the components of the needle assembly. When the barrier arm is positioned in the aperture it can move longitudinally with respect to the aperture but cannot come out of aperture 99 through gap 110 without the use of excessive force.

Like the embodiment of FIGS. 1–12, elongate barrier arm 100 is movable from at least a first retracted position, as best illustrated in FIG. 13, wherein distal end 82 of the distally facing needle cannula is exposed, to a second position, as best illustrated in FIG. 15, wherein the barrier element surrounds the distal end 82 and sharpened distal tip 83 of the needle cannula to prevent accidental contact with the distal end of the needle cannula.

Locking means is provided for preventing the movement of the barrier arm proximally from the second extended position of FIG. 15. Locking means includes proximally facing cantilever elements 110 and 111 configured to allow the barrier arm to pass through aperture 99 in the guide element in a distal direction but not in a proximal direction. As the elongate barrier arm is moved forward by applying distally directed digital pressure to contact surface 112, proximally facing cantilever elements enter the aperture and are forced into contact with the main body of the barrier arm until the elongate barrier arm moves to the second needle protecting position wherein the cantilever elements have passed completely through the aperture and snap outwardly to prevent proximal motion of the elongate barrier arm. The snapping outward motion of the cantilever elements also provides an audible indication to the user that the locking has taken place.

Needle assembly 77 also includes means for releasably holding the elongate barrier arm in the first retracted position. Means for releasably holding the needle barrel in the first position in this embodiment include protuberances 113 and 115 on the distal end of the barrier arm. The protuberances are shaped and sized so that distal force must be applied to the barrier element to force the portion of the barrier element containing the protuberances through the aperture.

Evacuated tube holder 79 includes a cylindrically-shaped barrel portion 116 with an open proximal end 117. In use distal end 82 of the cannula is placed into the patient's artery by urging the needle cannula in a distal direction until the sharpened distal tip pierces the artery and causes blood to flow through the lumen of the needle cannula. A cylindrically-shaped evacuated glass tube having a closed proximal end and a rubber stoppered distal end is placed in the open proximal end of the evacuated tube holder and urged distally until tip 88 of proximally facing needle 87 pierces the stopper and establishes fluid communication between the evacuated tube and the lumen of the inwardly facing needle cannula to draw blood from the patient's vein through needle cannula 80, hub 86, needle cannula 87 and into the evacuated tube. The tube can be removed from the holder and taken for laboratory analysis. The needle assembly may be withdrawn from the patient's vein and the digital pressure applied to contact surface 112 to advance the elongate barrier arm to the second extended needle protecting position. At this time the entire assembly of the tube holder and needle assembly may be discarded. Also, the needle assembly may be unscrewed from the tube holder so that the tube holder may be used again. Installing or removing the needle assembly from the tube holder involves rotating the hub so that the threaded portion of the needle hub moves along the internal threads 119 of the tube holder. Hub tab 118 on needle hub 86 is provided so that rotational force is applied to guide element 95 the guide element will rotate around the needle hub until portions of the guide element contact hub tab 118 and then the needle hub and the guide element will rotate in the desired direction for installation or removal of the needle assembly from the tube holder.

Also in drawing blood it is desirable to have the needle oriented so that the beveled cutting edge 85 faces outwardly and the needle is advanced at a shallow angle into the patient's vein. During this procedure it is desirable to have the barrier arm on the same side of the needle cannula as the beveled edge, as illustrated in FIG. 13 so that the barrier arm does not interfere with the shallow angle insertion of a needle into the vein. In this embodiment, the barrier arm may be rotated with respect to the needle cannula so that it is properly positioned to not interfere with the venipuncture. Also if the barrier arm is properly oriented before the start of the procedure the easily visible barrier arm acts as a guide to the medical technician indicating the orientation of the needle bevel.

It can be seen that the present invention provides a simple, inexpensive, reliable, easily fabricated needle assembly having a single-handedly activatable needle barrier which is self-contained and can be used with a variety of medical instruments. The present invention also provides a needle barrier which may be assembled from the side of a needle cannula without passing over the sharp and delicate needle tip.

What is claimed is:

1. A needle assembly having a single-handedly activatable needle barrier comprising:

a needle cannula having a proximal end, a distal end and a lumen therethrough;

a needle hub having an interior cavity terminating at an open proximal end of said hub, said hub connected to said needle cannula so that said lumen is in fluid communication with said interior cavity;

a guide element connected to said needle hub having an aperture therethrough;

an elongate barrier arm having a proximal end and a distal end, said distal end of said barrier arm including a barrier element having a distal end, a proximal end and a needle passageway therethrough, said barrier arm positioned within said aperture of said guide element and said needle cannula positioned at least partially within said needle passageway of said barrier element, said barrier arm being movable from at least a first retracted position wherein said distal end of said cannula passes completely through said barrier element so that said distal end of said needle cannula is exposed, to a second extended position wherein said barrier element surrounds said distal end of said cannula to prevent incidental contact with said distal end of said cannula;

locking means for preventing the movement of said barrier arm from said second extended position, said locking means being activated by movement of said barrier arm into said second extended position;

and finger contact surface on said barrier arm for applying digital pressure to said barrier arm to move said barrier arm into said second extended position.

2. The needle assembly of claim 1 wherein said guide element is integrally formed with said needle hub into a one-piece structure.

3. The needle assembly of claim 1 wherein said elongate barrier arm integrally formed with said barrier element into a one-piece structure.

4. The needle assembly of claim 1 wherein said locking means includes a projection on said barrier arm configured to allow said barrier arm to pass through said aperture of said guide element in a distal direction but not in a proximal direction.

5. The needle assembly of claim 4 when said projection is wedge-shaped being larger at its proximal end than at its distal end.

6. The needle assembly of claim 1 having means for releasably holding said barrier arm in said first retracted position.

7. The needle assembly of claim 6 wherein said means for releasably holding said barrier arm in said first retracted position includes a protuberance on said distal end of said barrier arm said protuberance being shaped to pass distally through said aperture of said guide means upon the application of distally directed digital force to said barrier arm.

8. The needle assembly of claim 6 wherein said means for releasably holding said barrier arm in said first retracted position includes said barrier arm having an enlarged cross-sectional dimension at its distal end so that the enlarged portion of said barrier arm frictionally engages said aperture in said guide element when said barrier arm is in said first retracted position.

9. The needle assembly of claim 1 wherein said locking means includes a metal clip contained by said barrier element, said clip having a transverse portion which is biased to contact the side of said cannula until said barrier arm reaches its second extended position wherein said transverse portion of said clip falls into a position at least partially covering said distal end of said needle and preventing movement of said barrier element in a proximal direction with respect to said needle cannula.

10. The needle assembly of claim 9 wherein said locking means further includes a projection on said barrier arm capable of passing through said aperture of said guide element in a distal direction but not in a proximal direction.

11. The needle assembly of claim 1 wherein said guide element comprises a cap and a main body connected together to define said aperture.

12. A needle assembly having a single-handedly activatable needle barrier comprising:

a needle cannula having a proximal end, a distal end and a lumen therethrough;

a needle hub having an interior cavity terminating at an open proximal end of said hub, said hub connected to said needle cannula so that said lumen is in fluid communication with said interior cavity;

a guide element connected to said needle hub having an aperture therethrough, said guide element including a cap and a main body connected together to define said aperture, said cap being hingedly connected to said main body so that said cap can be rotated about said hinge into contact with said main body to define said aperture;

an elongate barrier arm having a proximal end and a distal end said distal end of said barrier arm including a barrier element having a distal end, a proximal end and a needle passageway therethrough, said barrier arm positioned within said aperture of said guide element and said needle cannula positioned at least partially within said needle passageway of said barrier element, said barrier arm being movable from at least a first retracted position wherein said distal end of said cannula passes completely through said barrier element so that said distal end of said needle cannula is exposed, to a second extended position wherein said barrier element surrounds said distal end of said cannula to prevent incidental contact with said distal end of said cannula;

locking means for preventing the movement of said barrier arm from said second extended position;

and finger contact surface on said barrier arm for applying digital pressure to said barrier arm to move said barrier arm into said second extended position.

13. The syringe assembly of claim 1 wherein said barrier element contains a first longitudinal slot extending outwardly from said needle passageway.

14. A needle assembly having a single-handedly activatable needle barrier comprising:

a needle cannula having a proximal end, a distal end and a lumen therethrough;

a needle hub having an interior cavity terminating at an open proximal end of said hub; said hub connected to said needle cannula so that said lumen is in fluid communication with said interior cavity;

a guide element connected to said needle hub having an aperture therethrough;.

an elongate barrier arm having a proximal end and a distal end, said distal end of said barrier arm including a barrier element having a distal end, a proximal end and a needle passageway therethrough, said barrier arm positioned within said aperture of said guide element and said needle cannula positioned at least partially within said needle passageway of said barrier element, said barrier arm being movable from at least a first retracted position wherein said distal end of said cannula passes completely through said barrier element so that said distal end of said needle cannula is exposed, to a second extended position wherein said barrier element surrounds said distal end of said cannula to prevent incidental contact with said distal end of said cannula;

said barrier element including a first longitudinal slot extending outwardly from said needle passageway, a second longitudinal slot opposed from said first longitudinal slot and extending outwardly from said needle passageway and a transverse slot connecting said first and said second longitudinal slots and extending outwardly from said needle passageway;

locking means for preventing the movement of said barrier arm from said second extended position;

and finger contact surface on said barrier arm for applying digital pressure to said barrier arm to move said barrier arm into said second extended position.

15. The needle assembly of claim 1 connected to a syringe barrel having an elongate cylindrical body defining a chamber for retaining fluid, an open proximal end, a distal end and a tip extending from said distal end having a tip passageway therethrough in fluid communication with said chamber, said tip of said syringe barrel being positioned in said cavity of said needle hub.

16. The needle assembly of claim 1 wherein said elongate barrier arm is made of transparent thermoplastic material.

17. The needle assembly of claim 1 wherein said distal end of said needle cannula includes a sharpened distal tip having a beveled cutting edge.

18. The needle assembly of claim 17 wherein said aperture of said guide element is positioned so that said elongate guide arm is on the same side of said needle cannula as said beveled edge.

19. The needle assembly of claim 1 wherein said needle hub is integrally formed with a syringe barrel having an elongate cylindrical body defining a chamber for retaining fluid, an open proximal end and a distal end, said needle being integrally formed with said distal end of said barrel so that said chamber and said lumen of said cannula are in fluid communication.

20. The needle assembly of claim 1 further including means for providing an audible indication when said elongate barrier arm is moved distally into said second extended position.

21. A needle assembly having a single-handedly activatable needle barrier comprising:.

a needle cannula having a proximal end, a distal end and a lumen therethrough;

a needle hub having an interior cavity terminating at an open proximal end of said hub, said hub connected to said needle cannula so that said lumen is in fluid communication with said interior cavity;

a guide element connected to said needle hub having an aperture therethrough, said guide element being rotatably connected to said needle hub so that said guide element can rotate with respect to said needle cannula;

an elongate barrier arm having a proximal end and a distal end, said distal end of said barrier arm including a barrier element having a distal end, a proximal end and a needle pasageway therethrough, said barrier arm positioned within said aperture of said guide element and said needle cannula positioned at least partially within said needle passageway of said barrier element, said barrier arm being movable from at least a first retracted position wherein said distal end of said cannula passes completely through said barrier element so that said distal end of said needle cannula is exposed, to a second extended position wherein said barrier element surrounds said distal end of said cannula to prevent incidental contact with said distal end of said cannula;

locking means for preventing the movement of said barrier arm from said second extended position;

and finger contact surface on said barrier arm for applying digital pressure to said barrier arm to move said barrier arm into said second extended position.

22. A needle assembly having a single-handedly activatable needle barrier comprising;

a needle cannula having a proximal end, a distal end and a lumen therethrough;

a needle hub having an interior cavity terminating at an open proximal end of said hub, said hub connected to said needle cannula so that said lumen is in fluid communication with said interior cavity;

a guide element connected to said needle hub having an aperture therethrough;.

an elongate barrier arm having a proximal end and a distal end, said distal end of said barrier arm including a barrier element having a distal end, a proximal end and a needle passageway therethrough, said barrier arm positioned within said aperture of said guide element and said needle cannula positioned at least partially within said needle passageway of said barrier element, said barrier arm being movable from at least a first retracted position wherein said distal end of said cannula passes completely through said barrier element so that said distal end of said needle cannula is exposed, to a second extended position wherein said barrier element surrounds said distal end of said cannula to prevent incidental contact with said distal end of said cannula;

said guide element including a gap positioned to intersect said aperture so that the portion of the guide element defining the aperture does not completely surround said elongate barrier arm;

locking means for preventing the movement of said barrier arm from said second extended position;

and finger contact surface on said barrier arm for applying digital pressure to said barrier arm to move said barrier arm into said second extended position.

23. The needle assembly of claim 22 wherein said gap and said elongate barrier arm are configured so that said barrier arm may be laterally snapped into said aperture during assembly.

24. The needle assembly of claim 1 wherein said open proximal end of said hub is defined by a proximally facing needle cannula having a lumen therethrough and connected so that said lumen of said proximally facing needle cannula is in fluid communication with said needle cannula.

25. The needle assembly of claim 24 wherein said needle cannula, said cavity of said hub, and said proximally facing needle cannula comprise a single needle cannula passing through said hub.

26. A method of assembling a single-handedly activatable needle barrier comprising the steps of:

a. providing a needle assembly including a needle cannula having a proximal end, a distal end and a lumen therethrough, a needle hub having an interior cavity terminating at an open proximal end of said hub, said hub connected to said needle cannula so that said lumen is in fluid communication with said interior cavity, a guide element connected to said needle hub and capable of forming an aperture therethrough, said guide element comprising a cap and a mean body connected together for defining said aperture;

b. providing a barrier arm having a proximal end and a distal end, said distal end of said barrier arm including a barrier element having a distal end, a proximal end and a needle passageway therethrough, said barrier arm being dimensioned so that when said barrier arm is positioned within said aperture of said guide element said needle cannula is positioned at least partially within said passageway of said barrier element, said barrier element including a first longitudinal slot extending outwardly from said needle passageway, the second longitudinal slot opposed from said first longitudinal slot and extending outwardly from said needle passageway and a transverse slot connecting said first and second longitudinal slots and extending outwardly from said needle passageway;

c. orienting said needle assembly and said barrier arm so that said needle cannula is positioned within said transfer slot of said barrier element;

d. rotating said needle assembly and said elongate barrier element so that said needle cannula passes through said first longitudinal slot and said second longitudinal slot and is positioned within said needle passageway of said barrier element and said barrier arm is adjacent to said guide element; and e. locking said cap to said main body around said barrier arm to form an aperture through which said barrier arm may pass in a distal direction.

27. The method of claim 26 wherein said cap is hingedly connected to said main body so that the cap may be rotated into a position to connect with said main body to form said aperture.

* * * * *